(12) United States Patent
Ni et al.

(10) Patent No.: US 6,461,874 B1
(45) Date of Patent: Oct. 8, 2002

(54) STABILIZATION OF PARTICLES AND REDUCTION OF SAMPLE DISCORDANCE IN IMMUNOASSAYS USING CASEIN COATING OF PARTICLES

(75) Inventors: Wei-Chao Ni, Foxboro; Daniel W. Eustace, North Attleboro; Steve Chin-Shen Chang, Franklin, all of MA (US)

(73) Assignee: Bayer Corporation, East Walpole, MA (US)

( * ) Notice: Subject to any disclaimer, the term of this patent is extended or adjusted under 35 U.S.C. 154(b) by 0 days.

(21) Appl. No.: 09/491,139

(22) Filed: Jan. 26, 2000

Related U.S. Application Data

(60) Provisional application No. 60/117,578, filed on Jan. 27, 1999.

(51) Int. Cl.[7] .............................................. G01N 33/553
(52) U.S. Cl. ........................ 436/526; 436/531; 436/534; 436/810; 436/548; 435/7.9; 435/188; 435/963; 435/176; 435/180; 427/414; 427/337; 427/338; 427/222; 427/2; 428/403; 428/407; 530/815
(58) Field of Search .................................. 436/526, 531, 436/534, 810, 548; 435/7.9, 188, 963, 176, 180; 427/414, 337, 338, 222, 2; 428/403, 407; 530/815

(56) References Cited

U.S. PATENT DOCUMENTS

| | | | |
|---|---|---|---|
| 4,075,196 A | * 2/1978 | Badertscher et al. | 260/120 |
| 4,096,586 A | * 6/1978 | Badertscher et al. | 366/136 |
| 4,459,361 A | 7/1984 | Gefter | 436/523 |
| 4,554,088 A | 11/1985 | Whitehead et al. | 252/62.54 |
| 4,618,502 A | * 10/1986 | Beach | 426/583 |
| 4,628,037 A | 12/1986 | Chagnon et al. | 436/526 |
| 4,812,414 A | 3/1989 | Warren, III et al. | 436/533 |
| 4,828,980 A | 5/1989 | Snyder et al. | 435/7 |
| 4,842,758 A | * 6/1989 | Crutzen | 252/8.7 |
| 5,091,318 A | * 2/1992 | Anawis et al. | 436/513 |
| 5,126,242 A | * 6/1992 | Hachmann et al. | 435/7.9 |
| 5,132,208 A | 7/1992 | Freitag et al. | 435/7.1 |
| 5,164,299 A | * 11/1992 | Lambert | 435/7.92 |
| 5,445,936 A | 8/1995 | Piran et al. | 435/6 |
| 5,480,872 A | * 1/1996 | Cope et al. | 514/21 |
| 5,541,072 A | 7/1996 | Wang et al. | 435/7.21 |
| 5,635,363 A | * 6/1997 | Altman et al. | 435/7.24 |
| 5,639,626 A | * 6/1997 | Kiaei et al. | 435/7.92 |
| 5,677,133 A | * 10/1997 | Oberhardt | 435/7.1 |
| 5,705,338 A | 1/1998 | Piran et al. | 435/6 |
| 5,710,006 A | * 1/1998 | Kiaei et al. | 435/6 |
| 5,851,777 A | * 12/1998 | Hunter et al. | 435/7.1 |
| 5,928,958 A | 7/1999 | Pilgrimm | 436/526 |
| 5,939,272 A | * 8/1999 | Buechler et al. | 435/7.1 |

FOREIGN PATENT DOCUMENTS

| EP | 0369361 | 5/1990 | G01N/33/543 |
|---|---|---|---|

* cited by examiner

*Primary Examiner*—Christopher L. Chin
*Assistant Examiner*—Pensee T. Do
(74) *Attorney, Agent, or Firm*—Weingarten, Schurgin, Gagnebin & Lebovici LLP

(57) ABSTRACT

It has been found that casein and salts of casein are useful as replacements for, or in addition to, BSA as materials for coating solid phases, particularly magnetic particles, used in immunoassays and other binding assays for separation of the desired analyte. By using casein, immunoassays having improved stability and fewer discordant samples have been developed. Casein used at a concentration of 0.05–4.0 grams per gram of paramagnetic particle (optimally approximately 0.78–1.2 grams of casein per gram of magnetic particle) has been found to confer this benefit.

10 Claims, 11 Drawing Sheets

ACS:180 ThCG Solid Phases - 37°C Stability

| Chiron Lig Control | Control Solid Phase 0.08 g BSA / g PMP | | | Modified Solid Phase 1 g Casein + 0.08 g BSA / g PMP | | |
|---|---|---|---|---|---|---|
| | RLU | | % Recovery wrt Day 0 | RLU | | % Recovery wrt Day 0 |
| | Day 0 | Day 14 | | Day 0 | Day 14 | |
| 9761063 | 13331 | 9855 | 73.9 | 10315 | 9430 | 91.4 |
| 9762063 | 43134 | 33654 | 78.0 | 34951 | 31779 | 90.9 |
| 9763063 | 417489 | 302001 | 72.3 | 349680 | 285432 | 81.6 |
| 9761071 | 14300 | 10047 | 70.3 | 10867 | 9790 | 90.1 |
| 9762071 | 28003 | 20857 | 74.5 | 22336 | 19673 | 88.1 |
| 9763071 | 352662 | 270656 | 76.7 | 316818 | 255631 | 80.7 |
| Mean | | | 74.3 | | | 87.1 |

*Table 1*

ADVIA Centaur TUp Simulated On-Board Stability Study

| Chiron Ligand Controls | | Day 0 | | | |
|---|---|---|---|---|---|
| | | Present | | Modified | |
| | | RLU | TU Ratio | RLU | TU Ratio |
| 9761071 | 0.77 - 1.19 | 217213 | 1.04 | 136931 | 1.06 |
| 9762071 | 0.99 - 1.51 | 176143 | 1.26 | 108564 | 1.33 |
| 9763071 | 1.30 - 1.98 | 132623 | 1.70 | 80358 | 1.80 |

| Control | Day 3 | | | | | | Day 7 | | | | | |
|---|---|---|---|---|---|---|---|---|---|---|---|---|
| | Present | | | Modified | | | Present | | | Modified | | |
| | RLU | TU Ratio | % Rec | RLU | TU Ratio | % Rec | RLU | TU Ratio | % Rec | RLU | TU Ratio | % Rec |
| 9761071 | 196681 | 1.15 | 110.3 | 134373 | 1.07 | 101.2 | 190801 | 1.18 | 113.9 | 135095 | 1.07 | 101.1 |
| 9762071 | 151770 | 1.48 | 115.9 | 107260 | 1.34 | 101.0 | 151572 | 1.49 | 116.0 | 107824 | 1.34 | 101.1 |
| 9763071 | 113409 | 1.99 | 116.9 | 80287 | 1.80 | 100.0 | 114639 | 1.96 | 115.6 | 78584 | 1.84 | 102.4 |

| Control | Day 10 | | | | | | Day 14 | | | | | |
|---|---|---|---|---|---|---|---|---|---|---|---|---|
| | Present | | | Modified | | | Present | | | Modified | | |
| | RLU | TU Ratio | % Rec | RLU | TU Ratio | % Rec | RLU | TU Ratio | % Rec | RLU | TU Ratio | % Rec |
| 9761071 | 172986 | 1.30 | 125.4 | 129944 | 1.11 | 104.8 | 166385 | 1.35 | 129.8 | 122499 | 1.18 | 111.3 |
| 9762071 | 138110 | 1.63 | 127.5 | 101831 | 1.42 | 106.8 | 131601 | 1.71 | 133.6 | 97931 | 1.46 | 111.3 |
| 9763071 | 103776 | 2.17 | 127.9 | 74889 | 1.93 | 107.3 | 99970 | 2.25 | 132.4 | 72412 | 2.00 | 111.1 |

| Control | Day 22 | | | | | | Day 28 | | | | | |
|---|---|---|---|---|---|---|---|---|---|---|---|---|
| | Present | | | Modified | | | Present | | | Modified | | |
| | RLU | TU Ratio | % Rec | RLU | TU Ratio | % Rec | RLU | TU Ratio | % Rec | RLU | TU Ratio | % Rec |
| 9761071 | 169901 | 1.33 | 127.9 | 123569 | 1.17 | 110.4 | 167356 | 1.33 | 127.9 | 119414 | 1.21 | 114.2 |
| 9762071 | 136337 | 1.65 | 128.9 | 97964 | 1.47 | 110.5 | 139312 | 1.62 | 126.6 | 95585 | 1.51 | 113.5 |
| 9763071 | 104469 | 2.16 | 127.1 | 72755 | 1.99 | 110.6 | 103832 | 2.17 | 127.6 | 71668 | 2.02 | 112.2 |

*Table 2*

ACS: 180 TUp Performance Data

| | Present | Modified |
|---|---|---|
| Precision, (n = 10) | CV % | |
| TU Ratio 0.98 | 2.41 | 1.09 |
| 0.125 | 1.98 | 2.74 |
| 0.164 | 0.82 | 2.08 |
| Control Recoveries | TU Ratio | |
| Chiron Ligands   TU Ratio 9761071     0.77 - 1.19 | 1.02 | 1.02 |
| 9762071     0.99 - 1.51 | 1.28 | 1.31 |
| 9763071     1.30 - 1.98 | 1.66 | 1.74 |

*Table 3*

ACS: 180 T4 Performance Data
| Specification | Present | Modified |
|---|---|---|
| Least Detectable Dose, 0.5 ug/dl | 0.24 | 0.18 |
| % Bo/TC: ≥ 18 | 24.8 | 20.6 |
| ED50 : 3.79 - 4.83 ug/dl | 4.82 | 4.17 |
| Cal High / Cal Low : 0.10 - 0.55 | 0.290 | 0.256 |
| S2 RLU / S6 RLU : 7.71 - 10.3 | 7.70 | 9.55 |
| Total Counts, RLU | 3282492 | 3282492 |
| Precision, ( n = 10 ) | CV% | |
| ug/dl | | |
| 1.12 | 26.5 | 9.33 |
| 4.73 | 3.85 | 3.10 |
| 10.1 | 1.66 | 1.58 |
| 19.0 | 2.26 | 4.98 |
| Control Recoveries | T4, ug/dl | |
| Lot    Range, ug/dl | | |
| 9761063    4.0 - 6.0 | 4.84 | 4.91 |
| 9762063    8.5 - 10.5 | 9.22 | 9.00 |
| 9763063    15.3 - 19.9 | 15.4 | 15.6 |
| 9761071    2.5 - 5.1 | 3.48 | 3.92 |
| 9762071    5.3 - 8.9 | 6.99 | 6.95 |
| 9763071    10.3 - 16.7 | 14.1 | 14.5 |
| Mastercurve, ug/dl | RLU | |
| 0 | 813787 | 676287 |
| 1.12 | 675847 | 560528 |
| 5.01 | 391975 | 291768 |
| 10.06 | 217109 | 149196 |
| 15.1 | 144808 | 99469 |
| 25.3 | 87740 | 58658 |
| 36.7 | 59543 | 38585 |
| Present | 0.1 g BSA/ g PMP | |
| Modified | 0.1 g BSA/ g PMP 1.0 g Casein/ g PMP | |
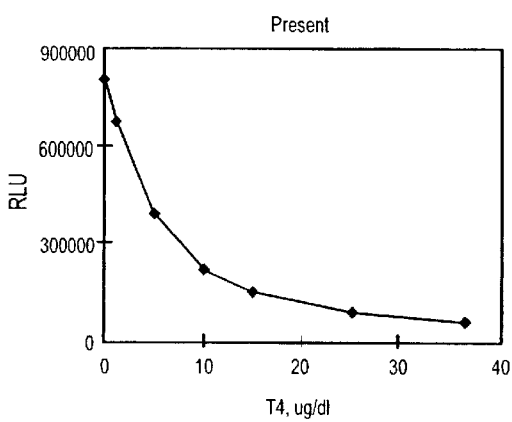
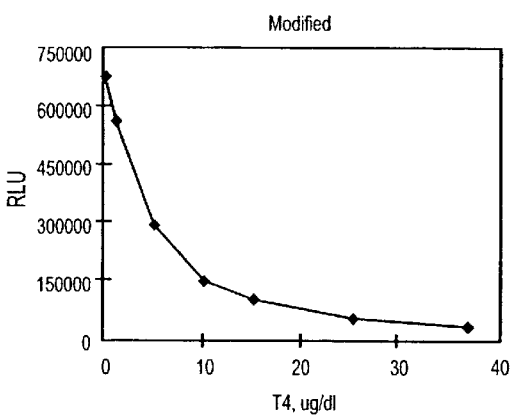
*Table 4*

ADVIA Centaur CA 19-9
37 °C Solid Phase Stability

| Level | U/mL | Day | With Casein ** | | Without Casein | |
|---|---|---|---|---|---|---|
| | | | RLU | RLU % Rec. | RLU | RLU % Rec. |
| 1 | 22.0 | 0 | 15544 | 100.0 | 23601 | 100.0 |
| | | 4 | 16400 | 105.5 | 12340 | 52.3 |
| | | 7 | 16043 | 103.2 | 12329 | 52.2 |
| | | 11 | 15568 | 100.2 | 12680 | 53.7 |
| | | 14 | 15174 | 97.6 | 12837 | 54.4 |
| | | Mean* | | 101.6 | | 53.2 |

| Level | U/mL | Day | With Casein ** | | Without Casein | |
|---|---|---|---|---|---|---|
| | | | RLU | RLU % Rec. | RLU | RLU % Rec. |
| 2 | 88.9 | 0 | 45080 | 100.0 | 52938 | 100.0 |
| | | 4 | 43273 | 96.0 | 38291 | 72.3 |
| | | 7 | 44524 | 98.8 | 37094 | 70.1 |
| | | 11 | 40778 | 90.5 | 38439 | 72.6 |
| | | 14 | 42190 | 93.6 | 36420 | 68.8 |
| | | Mean* | | 94.7 | | 71.0 |

| Level | U/mL | Day | With Casein ** | | Without Casein | |
|---|---|---|---|---|---|---|
| | | | RLU | RLU % Rec. | RLU | RLU % Rec. |
| 3 | 173 | 0 | 86516 | 100.0 | 98803 | 100.0 |
| | | 4 | 80469 | 93.0 | 76285 | 77.2 |
| | | 7 | 81352 | 94.0 | 73698 | 74.6 |
| | | 11 | 75595 | 87.4 | 72128 | 73.0 |
| | | 14 | 76487 | 88.4 | 70349 | 71.2 |
| | | Mean* | | 90.7 | | 74.0 |

\* Mean % Recovery of Days 4 - 14

\*\* 1.0 g Casein/g PMP

*Table 5*

STABILIZATION OF PARTICLES AND REDUCTION OF SAMPLE DISCORDANCE IN IMMUNOASSAYS USING CASEIN COATING OF PARTICLES

CROSS REFERENCE TO RELATED APPLICATIONS

This application claims priority under 35 U.S.C. 119(e) to U.S. Provisional Patent Application No. 60/117,578, filed Jan. 27, 1999, entitled STABILIZATION OF PARTICLES AND REDUCTION OF DISCORDANT SAMPLES IN IMMUNOASSAYS USING CASEIN COATING OF PARTICLES.

FIELD OF THE INVENTION

This invention relates to coated particles used in binding assays. It also relates to the process for making said particles and the process for using said particles.

BACKGROUND OF THE INVENTION

Binding assays, including immunoassays, are commonly used medical diagnostic tools for determining the presence, and the concentration, of various analytes. Immunoassay procedures have been known for many years and include the earlier manual procedures followed by the more recent automated procedures (e.g., those run on the Bayer ACS:180® and ADVIA® Centaur™ Instruments).

One of the components used in the immunoassays is a solid phase, frequently a paramagnetic particle (PMP), which is prepared by coating a magnetic particle with a material which allows further reaction of the magnetic particle with active ingredients used in the immunoassay. In the past, the magnetic particle has been frequently coated with bovine serum albumin (BSA). However, the particles coated with BSA have occasionally been found to be unstable and to yield unreliable assay results. In addition, the use of BSA alone results in high non-specific binding.

BRIEF SUMMARY OF THE INVENTION

It has been found that casein and salts of casein are useful as replacements for, or in addition to, BSA as materials for coating solid phases, particularly magnetic particles, used in immunoassays and other binding assays for separation of the desired analyte. By using casein, immunoassays having improved stability and less sample discordance have been developed. Casein used at a concentration of approximately 0.05–4.0 grams per gram of paramagnetic particle (optimally approximately 0.78–1.2 grams of casein per gram of magnetic particle) has been found to confer this benefit.

In addition, a process for coating solid phases has been invented, said process comprising the mixing of casein with magnetic particles at 30–60° C. for 5–180 hours, said process resulting in casein-coated paramagnetic particles which either (1) already have combined therewith active ingredients needed in the binding assay or (2) are capable of reacting with active ingredients needed in the binding assay.

Furthermore, a process for using the casein-coated paramagnetic particles has been developed, said particles being directly or indirectly combined with active ingredients used in the immunoassays.

Figures 1A, 1B:
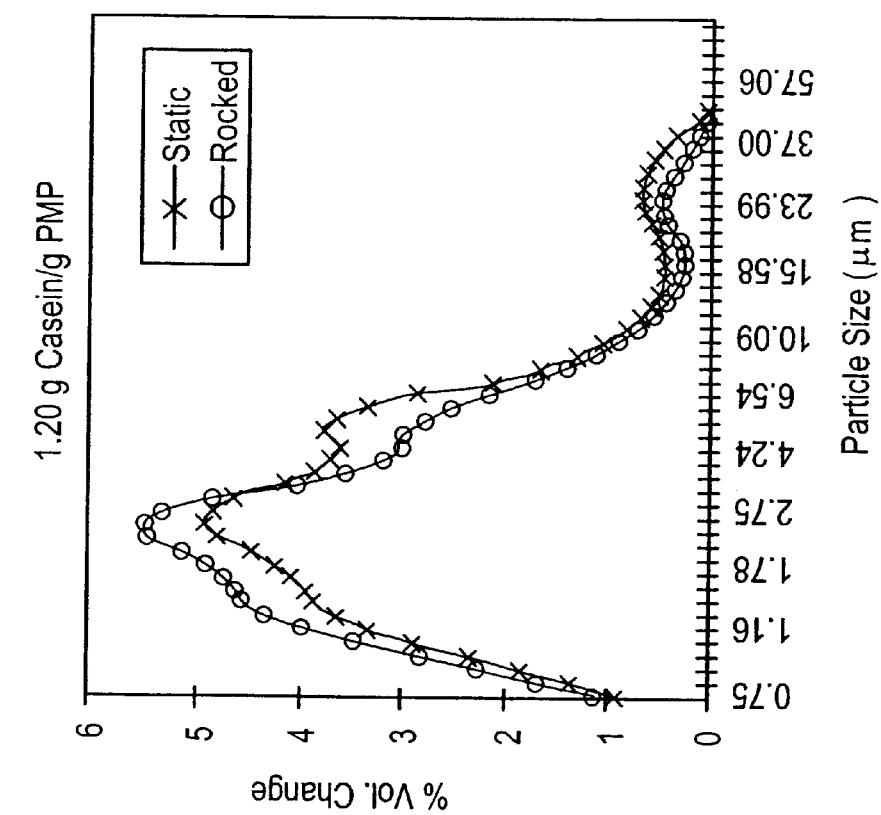
FIGS. 1a and 1b show particle size distribution (in % volume change vs. particle size) of the solid phase in the ferritin assay when 1.2 grams of BSA or casein per gram of PMP were used to coat the solid phase.

Tables 1–5 contain data referring to examples 1–4.

DETAILED DESCRIPTION OF THE INVENTION

Binding assays have been used for many years as a means for determining the presence of, and the concentration of, analytes when conducting medical diagnostic tests. The term binding assays is intended to cover a wide range of assays, including nucleic acid assays, gene probe assays, immunoassays, and membrane binding. In general, these assays incorporate the reaction of an analyte (or something that can be correlated with analyte concentration) with a solid phase, in order to separate the analyte from a solution, and reaction with a label that will allow detection of the analyte.

Two major types of immunoassays are competitive assays and non-competitive assays. In a competitive assay, the signal which is measured is that emanating from the specific binder that does not bind analyte. There are numerous formats of competitive assays. For example, in some competitive assays, the labeled antibody is incubated with a sample containing analyte and a solid phase-immobilized analyte derivative. The labeled antibody that did not bind analyte binds the solid phase, and the signal emanating from the solid phase-bound labeled antibody is measured. In other types of competitive assays, unlabeled antibody is incubated with a sample containing an analyte and a labeled analyte derivative (or analyte mimic). The labeled analyte derivative binds those antibody binding sites which are unoccupied. By measuring the signal coming from the labeled analyte derivative that bound the antibody, the chemist actually obtains an estimate of the concentration of antibody sites that did not bind analyte. Thus, in both types of competitive assays, one measures signal associated with the fraction of specific binder sites that did not bind analyte. The signal generated from a competitive assay decreases as the analyte concentration increases. Since small levels of analyte correspond to large signals, small changes in low concentrations of analyte lead to small differences between large numbers, which are hard to measure accurately.

A second type of binding assay is the non-competitive type. In this assay, a labeled specific binder, for example a labeled antibody, is incubated with the sample and binds a portion of the analyte. In one variation of non-competitive assay, a solid-phase immobilized unlabeled specific binder is added, simultaneously or in sequence, to bind another epitope on the analyte, in which case it is called a "sandwich" assay. For example, the immobilized molecule might be an antibody against a second epitope on the analyte, and the analyte might form a ternary complex with the labeled antibody and an immobilized unlabeled antibody. The solid phase is then washed and the signal measured is the signal that comes from the ternary complex containing the analyte. In this case the signal increases with increasing analyte concentration.

All of the assays discussed above are based on the use of a solid phase and a label that becomes attached (or bound or associated) with the solid phase. Many types of labels have been used in binding assays, for example radiochemical, luminescent, fluorescent, chemiluminescent, enzymatic, liposomal and various metal and non-metal particles. Preferably the label is a chemiluminescent label, such as an acridinium ester. The label can be attached directly to the binder by a covalent bond, or it can be indirectly attached using a binding pair, such as biotin/avidin, DNP/anti-DNP or any other binding pair.

The solid phase is generally separated from the reaction mixture at some stage of the process, and the amount of label attached to said solid phase is determined. The solid phase is generally made of particles made of controlled-pore glass, polymer particles, latex, colloidal metal or metal oxide particles, immiscible liquid phase, extended surface, porous paper, porous gel, liposome, lipos cellulose beads, emulsion, a system of very small particles that do not settle readily by standing or centrifugation, paramagnetic particles, cellulose beads, cross-linked dextran or any other particle. These can include particles that can vary in size from 10 nm to several microns in diameter, larger beads of any size, flat surfaces, test tube walls, dipstick surfaces, fibers, membranes, rods, discs, any extended or particulate surface capable of carrying an immobilized binder. A preferred solid phase is a magnetic particle or an extended surface.

The use of magnetic particles in assays involving separation steps has been known for some time. (See U.S. Pat. No. 4,554,088.) The magnetic particles frequently are reacted with intermediates (e.g., silanes and glutaraldehyde) in order to attach the biologically active component. Bovine serum albumin frequently has been used as one of these binding components.

In producing the magnetic particles, it was found that the instability was due to there being a thin coating of BSA on the PMP (i.e., low coating ratio of BSA to PMP). In addition, the BSA coated particles caused interference and sample discordance (i.e., incorrect assay results) in some assays.

It was found that casein, an inert protein, when used as a replacement for BSA or in addition to BSA, helped to eliminate the problems. When casein was used in the range of 0.05–4.0 grams of casein per gram of PMP, preferably in the range of 0.15–3.2 grams of casein per gram of PMP, and most preferably 0.78–1.2 grams of casein per gram of PMP, the problems were much reduced. The mixing of casein with the PMP took place at approximately 30–60° C. for 5–180 hours, preferably at approximately 37–50° C. for 14–144 hours. (A typical process for making casein-coated particles (used in the ferritin assay) is shown in Example 5. Variations of this process may be used when making solid phases for other assays.)

The particle stability was investigated by evaluating particle size distribution before and after rocking on an ADVIA® Centaur™ instrument. The rocking takes place when the reagents are mixed when the assay is run on the instrument. The casein-coated particles exhibited less aggregation or deaggregation due to particle interactions. Thus the casein is believed to have served as a cushion layer, which protected the particles from forming aggregates. See FIG. 1, which shows particle size distribution of the solid phase used in the Ferritin Assay, when rocked vs. static, said reagent being coated with 1.2 grams BSA/gram of PMP (FIG. 1a) or 1.2 grams casein/gram PMP (FIG. 1b).

Figure 3:
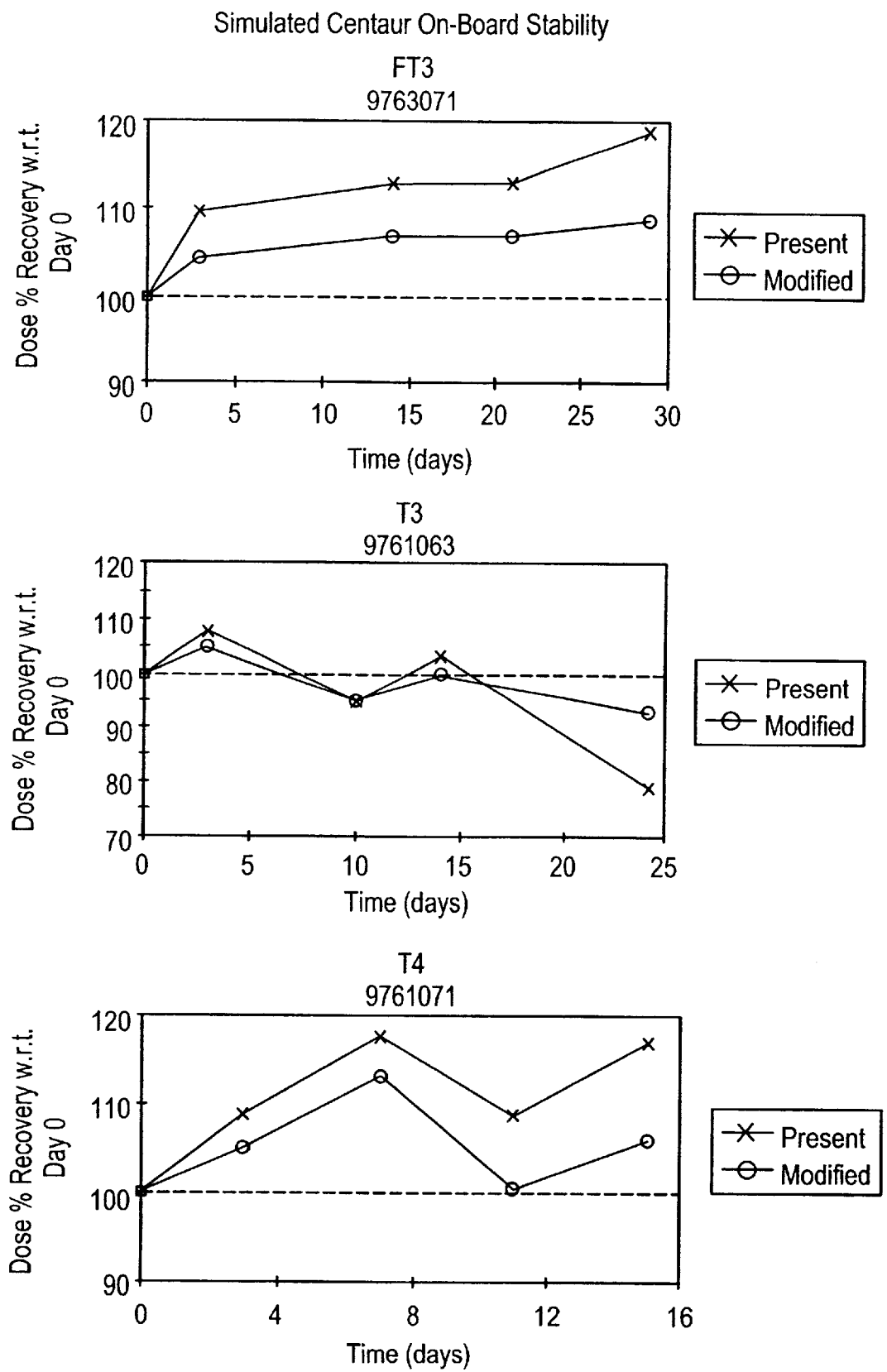
FIG. 3 shows Simulated On-Board Stability (in % dose recovery vs. time in days) for FT3, T3 and T4 for both BSA-coated magnetic particles (present) and casein-coated particles (modified).
Figure 4:
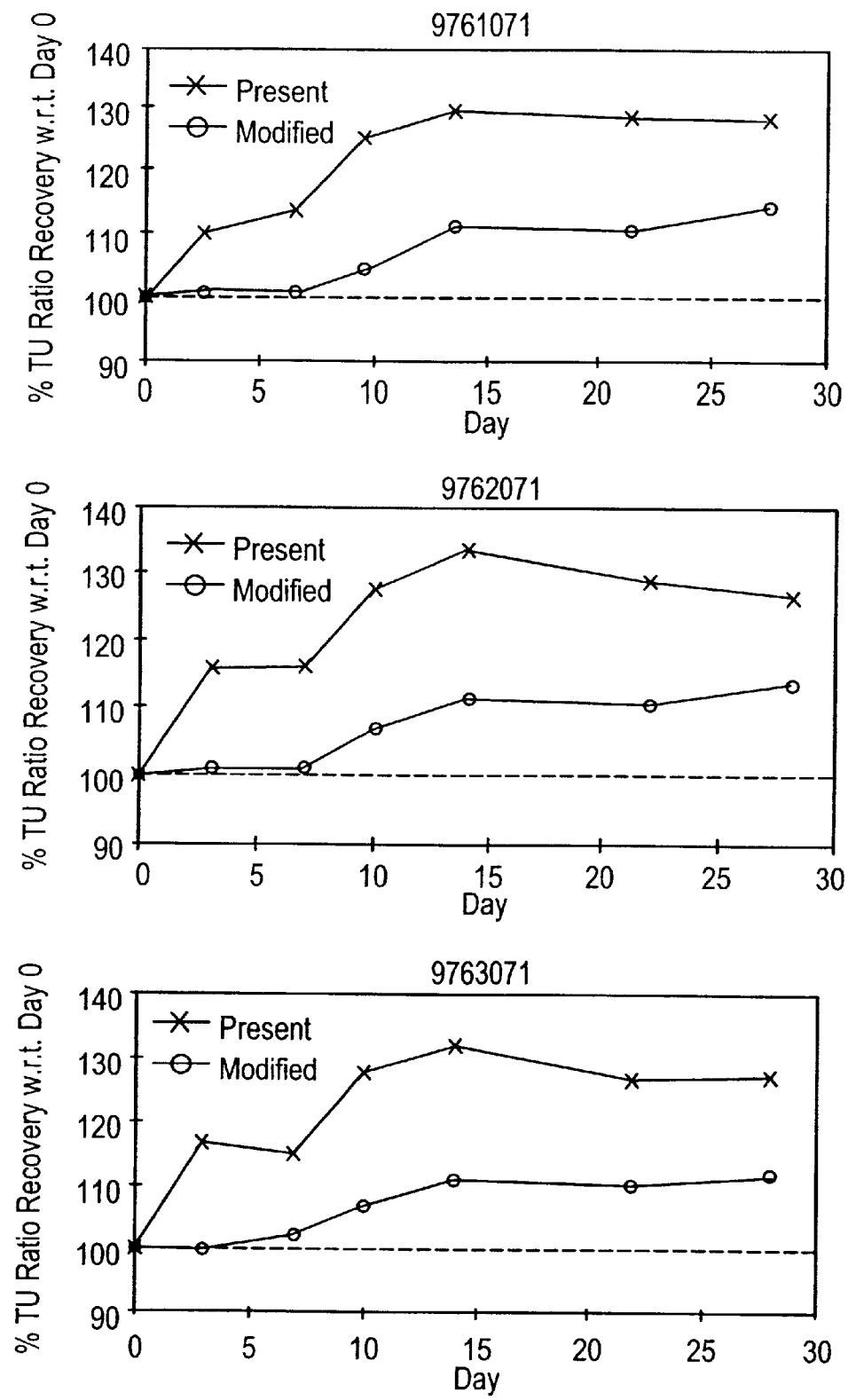
FIG. 4 shows Simulated On-Board Stability (in % TU Ratio recovery vs. time in days) for T-uptake for both BSA-coated magnetic particles (present) and casein-coated particles (modified).

Thermal stability was investigated with total human chorionic gonadotropin (ThCG), testosterone, CA 19-9 and free T3 and found to be significantly improved for the particles coated with casein. (See FIG. 2 and 6, Tables 1 and 5 and Example 1, below.) On-board stability and stored calibration stability (conducted as described below) were also found to be improved for T4, T3, free T3, and T-uptake. (See Example 2 (below), Table 2 and FIGS. 3–4.)

Stored calibration stability was investigated as follows. At day 0, a calibration point from the reagent formulations stored at 2–8° C. on an ADVIA® Centaur™ analyzer was assayed. A time-course study using the stored reagents was followed subsequently for 28 days. On a specific day, assays with both BSA-coated particles and casein-coated particles were performed. Each data point was compared to the day 0 stored calibration point for the corresponding reagent. The percent of dose recoveries of controls and patient sample pools with respect to day 0 was determined.

To conduct on-board stability tests, samples were stored in the refrigerated (2–8° C.) chamber of the ADVIA® Centaur™, which rocked the samples continuously. A sample was tested before the experiment began (day 0 value). Further samples were removed periodically (up to day 28) for analysis. The results were plotted vs. the data from day 0 to determine the effect of on-board storage on product performance.

Casein or its salts, such as sodium caseinate and potassium caseinate, have been found to be useful coating agents. The choice of form of casein depends, in part, on the medium in which the synthesis is conducted. For example, casein itself is hydrophobic and has relatively poor solubility in aqueous solutions. The salt sodium caseinate, on the other hand, has even better solubility in aqueous solutions, which leads, therefore, to higher concentrations of the caseinate in aqueous solutions and, subsequently, to thicker films of casein being deposited on the solid phase.

The use of BSA, the material generally used for coating solid phase particles, was responsible for interferences and non-specific binding. It is suspected that, since BSA had multiple binding sites for ligands, it allowed interferences by endogenous substances (i.e., those produced in humans), such as L-thyroxine, progesterone, testosterone, estradiol and cortisol. In addition, negatively charged drugs (such as ibuprofen and salicylate, etc.), neutral drugs (such as warfarin and iopanoate, etc.), positively charged drugs (such as quinidine, procaine and lidocaine, etc.), and inorganic ions (such as $Cu^+$, $Mn^{+2}$, $Ni^{+2}$, $Co^{+2}$, $Ca^{+2}$, and $Mg^{+2}$) have been found to cause interference.

The multiple binding sites on BSA can possibly result in sample discordance if the patient is being medicated with certain drugs. It is known that many drugs strongly bind to albumins. (See Ulrich Kragh-Hansen, 33 Pharmacological Reviews (1981) 17–53, Molecular Aspects of Ligand Binding to Serum Albumin.) Upon binding the drug molecules to BSA, there can be a triggering of side reactions on particles in addition to the expected antigen-antibody binding reaction. This can complicate the assay system and result in a false signal for sample discordance. Replacing BSA with inert casein on the particle surface can eliminate this problem. Even if the BSA is not totally eliminated, but the casein is the major coating agent (comprising at least 75% of the casein/BSA mixed coating), an improvement is observed.

Changing to casein as the coating material eliminated interferences from thyroid hormone, steroid hormone binding and other non-specific binding. For example, in the T4 assay, the change from BSA to casein resulted in the least detectable dose being reduced from 0.24 µ/dl to 0.18 µ/dl. Moreover, the precision at the low end of the assay (1.12 µ/dl) was significantly improved, and the coefficient of variation was improved from 26.5% to 9.3%.

Casein has been used previously in diagnostic assays, but not for coating particles and not for improving stability. In Snyder (U.S. Pat. No. 4,828,980), casein was used to coat membrane structures in order to prevent the non-specific binding of proteins to the membrane surface. In Warren (U.S. Pat. No. 4,812,414), particles which contain tracers (labels) were reacted with casein to reduce background signals from positively and negatively charged materials (see col. 2, lines 5–13, 57–60 therein). (I.e., it showed some benefit only when preventing charge-charge interaction.) The casein was not demonstrated to show any benefit with non-charged receptor molecules. In addition, Warren used the casein on the label phase (see claim 1 therein), and the casein was added simultaneously with the addition of antibody (see col. 13, lines 24–29 of '414). Freitag (U.S. Pat. No. 5,132,208) discloses test strips used in some immunoassays in which the solid component (a polyester fabric) is coated with a protein which is insoluble in the sample liquid under the test conditions. Casein was found to be useful in those assays, since it was found to be almost completely insoluble and allows the active reagent to be deposited on the casein-coated fabric.

It is believed that the use of casein will improve stability in all types of immunoassays, including those for thyroid-related assays (e.g., T-uptake, thyroxine (T4), 3, 3', 5-triiodothyronine (T3), free 3, 3', 5-triiodothyronine (free-T3)), anemia assays (e.g., ferritin), hormone assays (e.g., total human chorionic gonadotropin, testosterone), and cancer marker assays (e.g., CA19-9).

The following examples are intended to exemplify, but not limit, the invention.

Example 1

Thermal Stability

Figure 2:
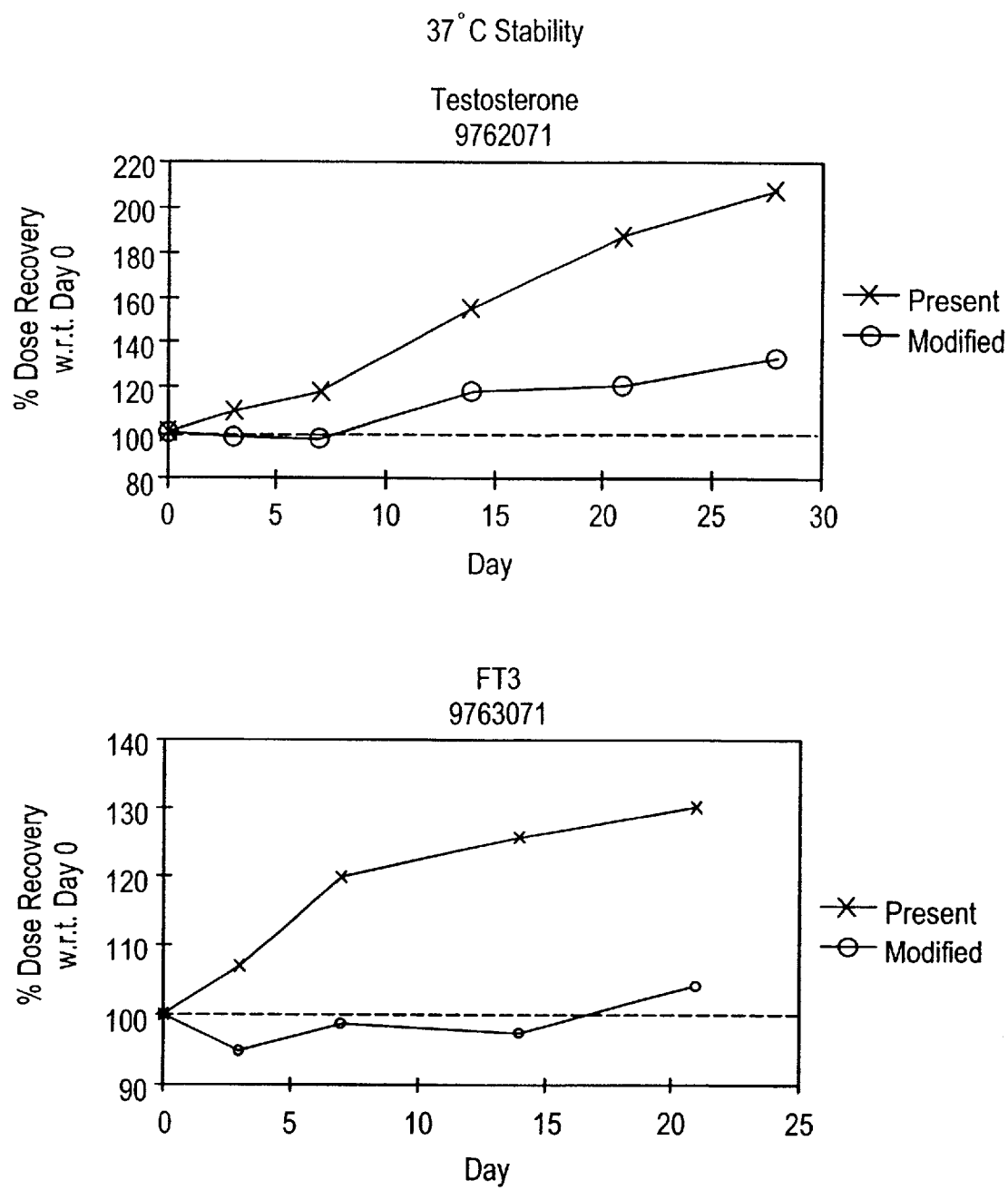
FIG. 2 shows stability at 37° C. (in % dose recovery vs. time in days) for both Testosterone and FT3 for both BSA-coated magnetic particles (present) and casein coated particles (modified).
Figure 6:
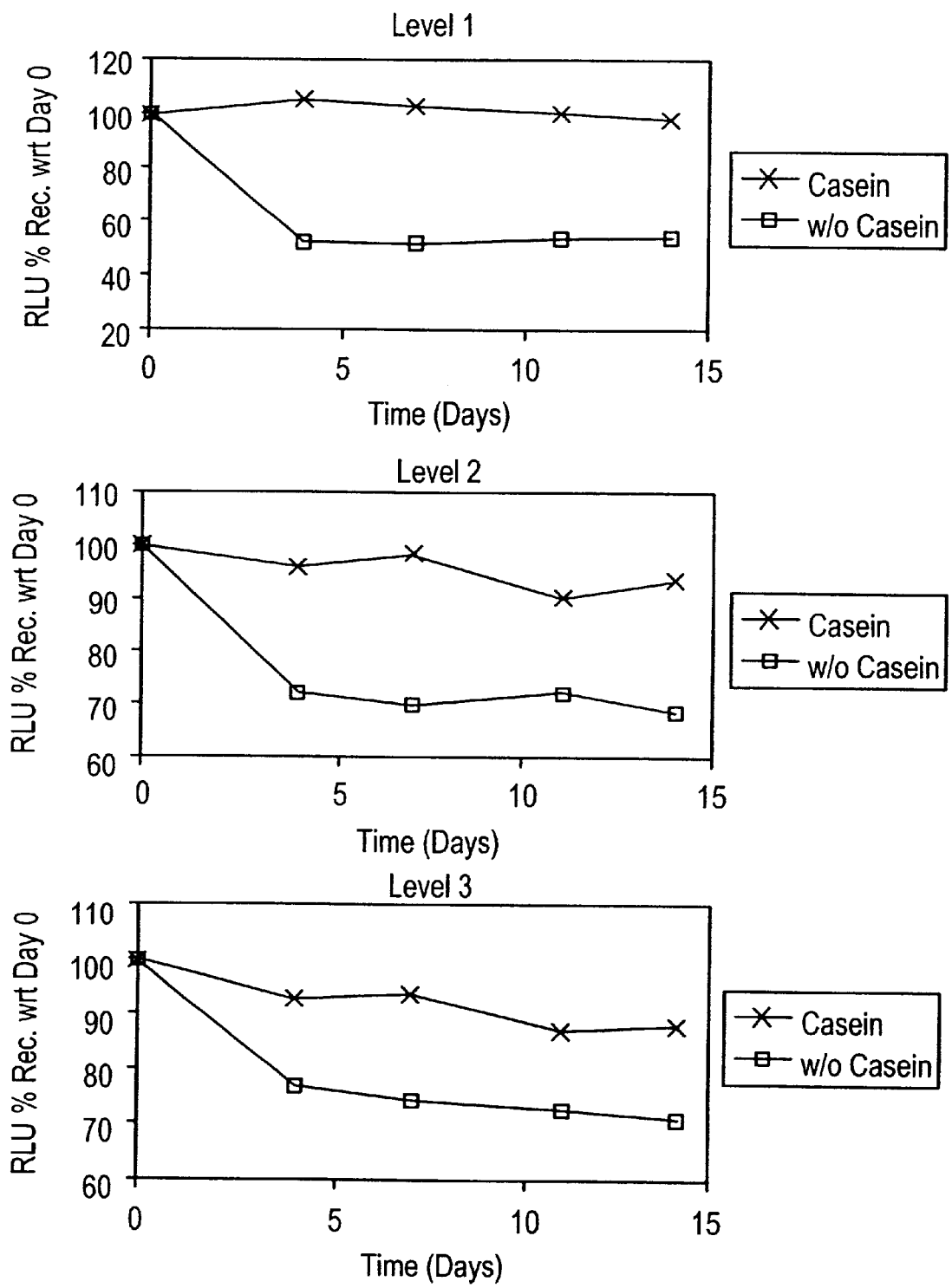
FIG. 6 shows solid phase stability at 37° C. for the CA 19-9 assay (in % dose recovery vs. time in days) for 3 different analyte levels for both BSA-coated magnetic particles (w/o casein) and casein coated-particles (casein).

Thermal stability of casein-coated particles at 37° C. were conducted by placing several bottles of reagent into an oven and removing one bottle at each test point for analysis. The use of the casein-coated particles showed a significant improvement, as shown by comparing the concentration of analyte determined as a function of time vs. the analyte concentration found at the beginning of the experiment. The results shown in FIG. 2 show that there is significant improvement with the casein-coated particle (referred to as "modified"). Stability in assays for testosterone and FT3 are shown in FIG. 2, while the data for stability in the ThCG assay is shown in Table 1. Thermal stability for CA 19-9 is shown in FIG. 6 and Table 5.

Example 2

On-Board Stability (Simulating Mixing in an Automated Instrument)

Figure 5:
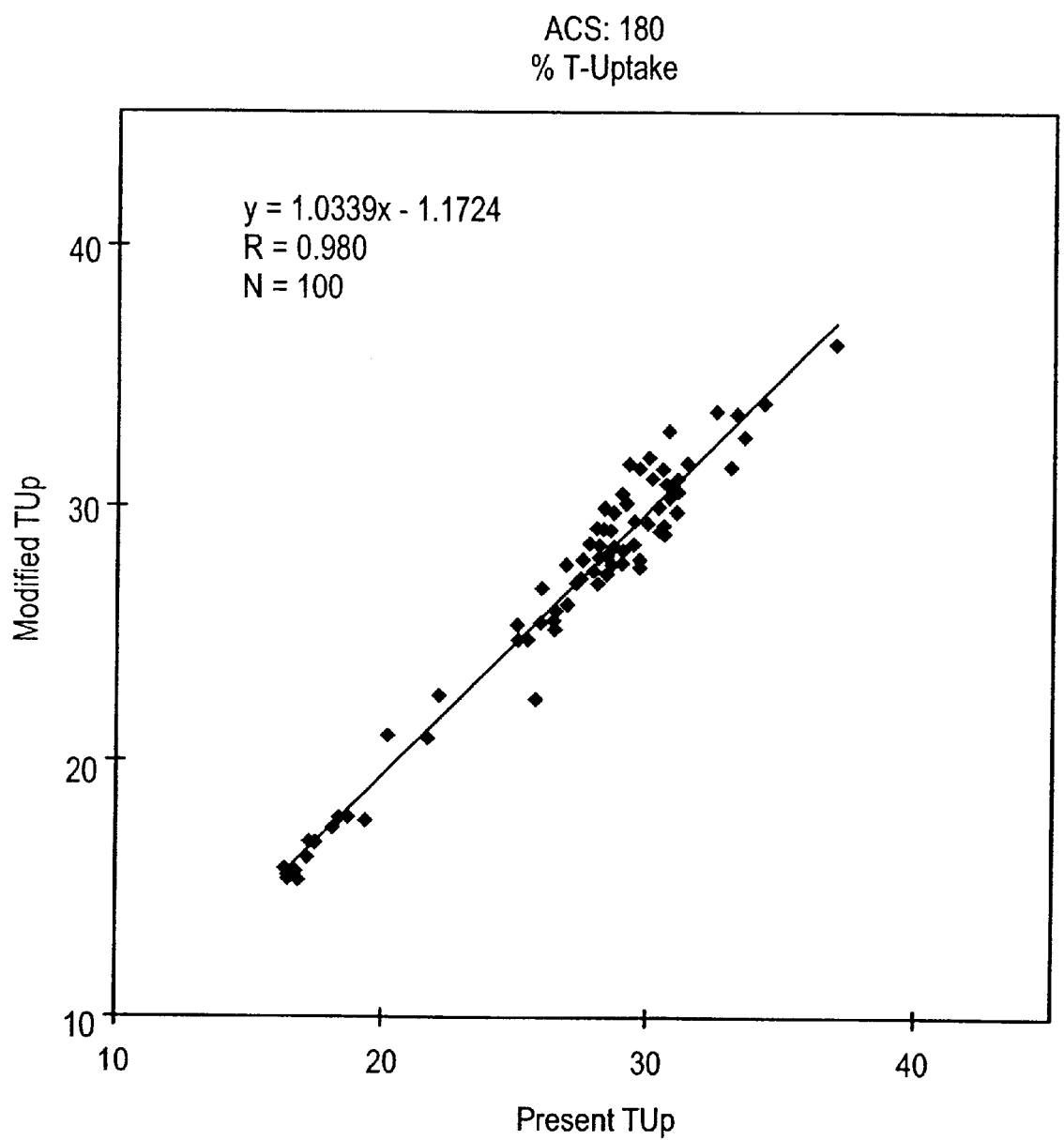
FIG. 5 is a correlation study showing % T-Uptake for 100 patient samples, each tested using the casein-coated solid phase (modified) vs. the BSA-coated solid phase (present).

On-board stability tests were conducted to determine the impact of casein coating. The on-board stability tests simulated the continuous mixing conducted by the ADVIA® Centaur™ instrument when the assay was conducted. See data in FIGS. 3 and 4 and in Table 2 for assay data from free T3, T3, T4 and T uptake data. The other assay performance criteria for T-uptake remained equivalent, as shown in FIG. 5 and Table 3.

Example 3

T4 Performance Test

A performance test was conducted using reagents for the T4 assay, with one version containing BSA coated onto PMP (see "Present" in Table 4) vs. PMP coated with casein ("Modified" in Table 4). See the improvement noted in Table 4 for Least Detectable Dose and Precision. In the other attributes, no change was noted between the BSA- and casein-coated solid phases, thus indicating that the casein-containing assay remained reliable. (Note that the "Modified" solid phase contained 0.1 g BSA and 1.0 g casein/g PMP.)

Example 4

CA 19-9 Stability

Stability in the assay for CA19-9, a cancer marker, has been significantly improved by the addition of casein to the solid phase used in that assay. See FIG. 6 and Table 5, which show the significantly improved stability at 3 analyte levels (22.0, 88.9, and 173 U/mL).

Example 5

Typical Process for Making Casein-coated Particles

1. PMP is activated by addition of 3.125% glutaraldehyde (in 0.01M sodium acetate, pH 5.5) which mixes for 3 hours at room temperature.

2. Antibody is coupled to the glutaraldehyde activated PMP, by adding 140 mg antibody/g PMP and reacting for 16.5 hours at room temperature while mixing.

3. The unreacted aldehyde is quenched by reaction with ethanolamine. The PMP's are magnetically separated by application of a magnetic force to the container. The particles are washed with 0.1 M sodium phosphate buffer (pH 8.0) and then resuspended in 0.1 M sodium phosphate buffer (pH 8.0). To the suspended particles is added ethanolamine (1.1M in the final reaction mixture), and the mixture is stirred for 1 hour at room temperature.

4. The Schiff base is reduced by addition of boranepyridine. The particles are separated via application of a magnetic field and are washed with 0.1 M sodium phosphate buffer (pH 8.0) and then resuspended in 0.1 M sodium phosphate buffer (pH 8.0). Borane-pyridine (borane-pyridine mixed with dimethyl sulfoxide at 1:4 vol/vol ratio), 50–100 mM in final reaction mixture, is added and allowed to react for 1 hour at room temperature.

5. The particles are separated via application of a magnetic force and washed with 1 M NaCl solution. The particles are washed with 0.01 sodium phosphate buffer (pH 8.0). The particles are washed with Heat Stress Buffer and then resuspended in Heat Stress Buffer, and the mixture is incubated at 50° C. for 16.5 hours. (Heat Stress Buffer consists of 0.220 g/L sodium phosphate (monobasic), 4.03 g/L sodium phosphate (dibasic), 8.75 g/L sodium chloride, 1 g/L sulfhydryl modified BSA, 0.010 g/L bovine gamma globulin (BgG), and 39 g/L casein (sodium salt), with a pH of 8.0.)

6. The particles are separated by application of a magnetic field and washed with 1 M NaCl, separated magnetically and washed with protein buffer. (The protein buffer consists of 0.220 g/L sodium phosphate (monobasic), 4.03 g/L sodium phosphate (dibasic), 8.75 g/L sodium chloride, 1 g/L sulfhydryl modified BSA, and 0.010 g/L BgG, with a pH of 8.0.) The resulting particles are resuspended in solid phase buffer (10 mM sodium barbital, 8.75 g/L sodium chloride, 0.095% sodium azide, 0.372 g/L disodium EDTA, 2.5 g/L gelatin, 1.0 g/L BgG, 3.0 g/L sulfhydryl modified BSA, 0.02 g/L mouse immunoglobulin G (IgG), 0.02 g/L caprine IgG, 0.2 mL/L amphotericin B, 0.48 mL/L gentamicin sulfate, 0.2% sodium cholate, and 0.05 g/L antifoam B, adjusted to pH 8.5).

Variations which are consistent with this invention will be apparent to those with skill in the art.

We claim:

1. A process for using solid phases coated with casein in binding assays, said solid phases being combined directly or indirectly to an active ingredient used in said binding assays, said process comprising
    a. mixing a measured aliquot of the sample to be analyzed with a measured amount of said coated solid phase,
    b. if said binding assay is a competitive assay, adding a measured amount of labeled analyte derivative, while, if said binding assay is a non-competitive assay, adding a labeled binding agent which binds to a second binding site on said analyte,
    c. separating said solid phase and determining the amount of label attached thereto, and
    d. determining the amount of analyte by comparing the amount of label to that on a reference curve generated by analyzing samples with known concentration of analyte,
    wherein said solid phase is coated with approximately 0.05–4.0 grams of casein per gram of solid phase.

2. The process of claim 1 in which said solid phase is a paramagnetic particle and said binding assay is an immunoassay or a gene probe assay.

3. The process of claim 2 in which said binding assay is for an analyte selected from the group consisting of ferritin; T-uptake; thyroxine; 3, 3', 5-triiodothyronine; free 3, 3', 5-triiodothyronine; total human chorionic gonadotropin; CA 19-9; and testosterone.

4. The process of claim 2, wherein said solid phase coated with casein reduces interference caused by non-specific binding.

5. The process of claim 2, wherein said solid phase coated with casein reduces interference caused by sample discordance.

6. The process of claim 2 in which stability is improved due to the addition of casein.

7. The process of claim 2, wherein said paramagnetic particle is coated with a mixture of casein and bovine serum albumin, said casein comprising at least 75% of said mixture.

8. The process of claim 1 in which said active ingredient is selected from the group consisting of antigens, antibodies, nucleic acids, nucleic acid polymers, and other receptors.

9. The process of claim 1 in which said casein is in the form of sodium caseinate or potassium caseinate.

10. The process of claim 1 wherein said solid phase is coated with approximately 0.78–1.2 grams of casein per gram of solid phase.

* * * * *